(12) United States Patent
Dobler

(10) Patent No.: US 7,700,665 B2
(45) Date of Patent: Apr. 20, 2010

(54) FRAGRANT GEL POLYMER SYSTEM

(75) Inventor: Sven Dobler, Huntington, NY (US)

(73) Assignee: Orlandi Inc., Farmingdale, NY (US)

(*) Notice: Subject to any disclaimer, the term of this patent is extended or adjusted under 35 U.S.C. 154(b) by 0 days.

(21) Appl. No.: 12/315,432

(22) Filed: Dec. 3, 2008

(65) Prior Publication Data

US 2009/0149566 A1 Jun. 11, 2009

Related U.S. Application Data

(60) Provisional application No. 61/005,737, filed on Dec. 6, 2007.

(51) Int. Cl.
*A61L 9/04* (2006.01)
*C08C 19/22* (2006.01)

(52) U.S. Cl. ............ 523/102; 525/374; 424/76.4; 264/299

(58) Field of Classification Search ........ 523/102; 424/76.4; 525/374
See application file for complete search history.

(56) References Cited

U.S. PATENT DOCUMENTS

| | | | | |
|---|---|---|---|---|
| 6,086,903 A | * | 7/2000 | Trinh et al. | 424/401 |
| 6,846,491 B1 | | 1/2005 | Richards | |
| 6,902,725 B2 | * | 6/2005 | Shah | 424/76.4 |
| 7,132,461 B2 | | 11/2006 | O'Leary et al. | |
| 2008/0015295 A1 | * | 1/2008 | Williams et al. | 524/236 |

* cited by examiner

*Primary Examiner*—Tae H Yoon
(74) *Attorney, Agent, or Firm*—Paul M Denk

(57) ABSTRACT

The fragrant gel polymer system is a process where a complete fragrance formulation remains whole and is then blended with either a polymer or a cross-linking agent. The non-fragrance carrying polymer is then liquefied and made homogenous with a solvent. The solvents modify viscosity and ease the mixing of the non-fragrance carrying polymer with the fragrance carrying polymer. The method also provides surfactants and wetting agents for further integration and mixing of the fragrance oils with either the polymer or the cross-linking agent during the steps of the process. Mixing of the fragrance carrying polymer and the non-fragrance polymer results in a gel that sets in less time and with less syneresis than existing processes.

2 Claims, 1 Drawing Sheet

FRAGRANT GEL POLYMER SYSTEM

CROSS-REFERENCE TO RELATED APPLICATION

This non-provisional application claims priority to the provisional application Ser. No. 61/005,737 with a filing date of Dec. 6, 2007, and is commonly owned by the same inventor.

BACKGROUND OF THE INVENTION

This fragrant gel polymer system relates to the manufacture of fragrant gels and more specifically to a process of mixing two fragrance components with two polymers. A unique aspect of the system is a reduction in syneresis and in testing requirements for reactivity between components of the system towards becoming a gel.

A variety of gel products are on the market, used mostly for toys, novelties, gifts, window clings, and decorative ornaments. Consumers are particularly attracted by the gel products due to their features of softness, color, and introduction of a scent or fragrance. These features, desired by consumers, are related to the nature of the gel product, which may contain mineral oil among other things. As mineral oil remains liquid at room temperatures, it may separate from the gel product when the gel product contracts slightly during syneresis. Additionally, the careful selection of the composition of gel products has improved related to the dispersion between a scent, or fragrance, and the surface of the gel products for introduction into the atmosphere.

A fragrant gel product results from the cross-linking between a functionalized polymer and a cross-linking agent, both generally liquid in the presence of a single or a multiple part fragrance base. The polymer cross-links in the presence of the fragrance to form a gel which encloses the perfume, or fragrance. The gel can form in a recess in a substrate as an air freshener device, as a block, and the like.

While mixing, the fragrance, polymer, and cross-linking agent forms a practical homogeneous mixture, such a mixture poorly controls the flow of the cross-linking agent in a small volume. For a better gel product, equalizing the flow rates of the different premixes into the final mixing step has had more positive results. Accordingly, the fragrance acquires a formulation by conventional methods and then a portion of the fragrance mixes with the polymer and the remainder of the fragrance mixes with the cross-linking agent. The two mixtures can then be mixed together to form a mixture that gels. As the fragrance remains separated within the two mixtures, the mixture containing the cross-linking agent has a greater volume than the volume of the cross-linking agent alone, and therefore a greater flow rate, more easily controlled.

Though this mixture method works well when the production line starts, the gel produced by the mixture method worsens after the production line has run for a time. The gelling time of the mixture, i.e. the time required for a non-flowing gel to form into a shape, tends to rise over time. This longer forming time causes problems into the manufacturing shift, especially at the end of a shift, on an operating machine. For example, if the gelling time of the mixture increases and exceeds the time that the containers, containing the fragrance elements, occupy the production line, the gel may have partially solidified and may retain some liquid when the containers, or forms, are removed from the production line. This liquid can spill from the forms, or containers, leading to waste of ingredients, disruption of the production line for cleaning, and release of spilled ingredients into the local sewage system.

Fragrances usually contain components which react with either, or both, of the functionalized polymer and the cross-linking agent. The prior art processes have the functionalized polymer and cross-linking agent each mixing with different parts of the fragrance, before the polymer and the cross-linking agent are mixed. Thus, the functionalized polymer and cross-linking agents mix with separate fragrance components, not the same fragrance composition. Instead, the gel product has a final fragrance composition arranged, and different components of the composition are then mixed with the functionalized polymer and with the cross-linking agent. By separating the fragrance components, the issue of incomplete gel formation decreases to a practical extent or even completely ceases.

While the precise ingredients of any particular fragrance often remain trade secrets, the typical classes of ingredients and particularly common ingredients include volatile compounds such as esters, alcohols, aldehydes and ketones. As before, the functionalized polymers and cross-linking agents react with certain fragrance ingredients but not others. The reaction rate may be relatively slow and that does not appear early in a manufacturing shift but, after the fragrance ingredients have been mixed with the functionalized polymer and cross-linking agent for some time, a few hours in many cases, some of the fragrance components will have reacted as a pre-reaction. Alas, these pre-reactions may undesirably affect the fragrance, varying its fragrance over a production run. Furthermore, the pre-reactions consume some of the functionalized polymer and cross-linking agent, thus reducing the concentration of reactive sites of the functionalized polymer and the cross-linking agent later in the production run. The pre-reactions have an often increased setting time using prior art methods and processes.

The functional polymer has one or more functional groups while the cross-linking agent has one or more complimentary functional groups. The mixture of these two provides, in the presence of a fragrance base, a reaction product that encloses the fragrance base in a gel product which then emanates the fragrance to the atmosphere to freshen the air. Suitable functional groups include carboxylic acid, anhydride or acid chloride groups, amines, and alcohols. The functional polymer forms by adding a functional group to any polymer capable of functionalization, or the polymer itself inherently contains functional groups. The functional groups can be pendent on the main chain perhaps with intervening spacer groups or in the main chain. Preferred polymers for functionalization include polyolefins, particularly those derived from mono-olefins or di-olefins containing, at least one vinyl group.

The cross-linking agent generally dissolves in the fragrance base. Suitable cross-linking agents include dihydroxy polybutadiene, alkoxylated primary amines, alkylpropyl-diamines having an ethoxylated or propoxylated fatty aliphatic chain, diethanolamine, diethylenetriamine, polyoxyalkylenediamines and alkoxylated primary fatty amines. The cross-linking agent may have one or more diamines or tri-amines, polyoxyalkylene amines, polyethoxy diamines and triamines, polypropoxy diamines and triamines.

Within the prior art, the fragrance is a mixture of volatile liquid ingredients of natural or synthetic origin. List and descriptions of the ingredients appear in perfumery books, for example in S. Arctander, *Perfume and Flavour Chemicals*, Montclair, N.J., USA, 1969, and the like. The art of formulating a fragrance begins with devising a base and at least a note having the desired fragrance, generally a common task carried out by a fragrance manufacturer.

Generally, the cross-linking agent reacts with some of the fragrance components, while the functionalized polymer does not appreciably react during a typical production shift.

The prior art separates the components of a fragrance into those components of the fragrance which react, or are likely to react, with the cross-linking agent and those components which do not react, or are unlikely to react. Individual fragrance components which do not react with either the functionalized polymer or the cross-linking agent may be mixed with either polymer or cross-linking agent at the discretion of the fragrance manufacturer.

DESCRIPTION OF THE PRIOR ART

Two main gel process patents guide the formulation and manufacture of gels. The first is U.S. Pat. No. 6,846,491 to Richards, which describes a clear polymeric gel of cross-linked polymers. For instance, the polymers include Lithene®, from Struktol Co. of America, Stow, Ohio, distributor for Synthomer® of the United Kingdom for Phase 1 and Jeffamine®, by Huntsman® Corp. of Salt Lake City, Utah for Phase 2. The fragrance begins as fragrant oil formulations of both organic and inorganic aroma chemicals along with other ingredients used to prepare fragrances. The fragrant oil formulations are blended with both Lithene® and Jeffamine® generally and with a surfactant such as Steol® by Stepan® Co. of Chicago, Ill. The fragrance oils pre-mix readily in Phases 1 and 2, thus making each phase homogeneous and fostering ready combination and mixture of Phases 1 and 2. The Richards method entraps the active aroma chemicals and produces a solid gel in less than 45 minutes. The Richards method also avoids the heat dependent formulations or those created at room temperature as known in the art. The heat dependent formulations run the risk of altering, modifying, or destroying the fragrance oils when the volatile organic compounds within the fragrance oils evaporate or break down.

Additionally, the polymers used by Richards have some high reactivity and react early with colorants and pigments during gel manufacturing. The polymers tend to lessen the ability of gels to remain color fast and in time, the gels lose their color. The polymers also react with aromatic chemicals in fragrance oil formulations thus partially depleting the aromatic chemicals before mixing with other fragrance components. The depleted aromatic chemicals lead to imperfect cross-linking of Lithene® and Jeffamine® polymers where the fragrance oils later precipitate from the gel, as in syneresis, or the gel becomes unstable, liquefies, and fails. Formulating fragrances for the Richards method has challenged manufacturers who have faced limits upon usage of fragrance components when creating various cosmetic products. In a few case, manufacturers have been thwarted in combining certain fragrances with gels.

The second gel process patent, U.S. Pat. No. 7,132,461 to O'Leary et al., applies a method of manufacturing fragrance oils making a fragrant gel in two parts. The O'Leary method splits the fragrance oils into two parts, the polymer reactive and the cross-linking agent reactive, such as Lithene® and Jeffamine® respectively. In splitting the oils, each element of a fragrance formulation requires testing for reactivity to various polymers for segregation into polymer and cross-linking agent reactive components. Generally, the polymer reactive parts are blended with cross-linking agent as Phase 1 while the cross-linking agent reactive parts are blended with polymer as phase 2. To form the complete fragrance, the two phases are blended and provide more effective cross-linking of polymers because the reactive sites of each polymer have not already reacted with the fragrance components known to favor that polymer. In blending the two phases, the fragrance components assemble and make the whole fragrance as desired by the consumer. The O'Leary method reduces syneresis and shrinkage of the gel product while improving the stability of the finished gel product.

The present invention overcomes the limitations of the prior art. That is, in the art of the present invention, a fragrant gel polymer system combines a fragrance formulation, a cross-linking agent, and a polymer in a certain sequence. The present invention blends the fragrance formulation with either a polymer or a cross-linking agent. The cross-linking agent or polymer not mixed with the fragrance formulation is then mixed with a solvent. Then the dissolved cross-linking agent or polymer is blended with the fragrance carrying polymer or cross-linking agent to form a gel of desired fragrance or consistency.

SUMMARY OF THE INVENTION

The preferred embodiment of the fragrant gel polymer system is a method where an entire fragrance formulation remains whole and is then blended with a polymer or a cross-linking agent, such as Lithene® and Jeffamine®, respectively, but not both. The method of the present invention reduces the premature reaction of the polymer and the cross-linking agent. The non-fragrance carrying polymer, or alternatively cross-linking agent, is then liquefied and made homogenous with a solvent. The solvents modify viscosity and ease the mixing of the non-fragrance carrying polymer with the fragrance carrying polymer. The method also provides surfactants and wetting agents for further integration and mixing of the fragrance oils with either the polymer, such as Lithene® or the cross-linking agent such as Jeffamine®. However, the invention is not limited to Lithene® and Jeffamine® usage.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

Therefore the object of the present invention is to provide a fragrant gel polymer system that reduces the formulation and testing requirements of constituent fragrances with polymers.

Another object of the fragrant gel polymer system is to allow for testing the constituent fragrances with any of the polymers.

Another object of the fragrant gel polymer system is to strengthen the color fastness and performance of a gel.

Another object of the fragrant gel polymer system is to reduce syneresis, gel instability, and product failure.

Another object of the fragrant gel polymer system is to reduce research and development efforts and costs commonly associated with two-part polymer and two-part split fragrance processes and formulations.

Another object of the present invention is to provide such a gel product that may be easily and efficiently manufactured and marketed at less cost than existing samplers.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
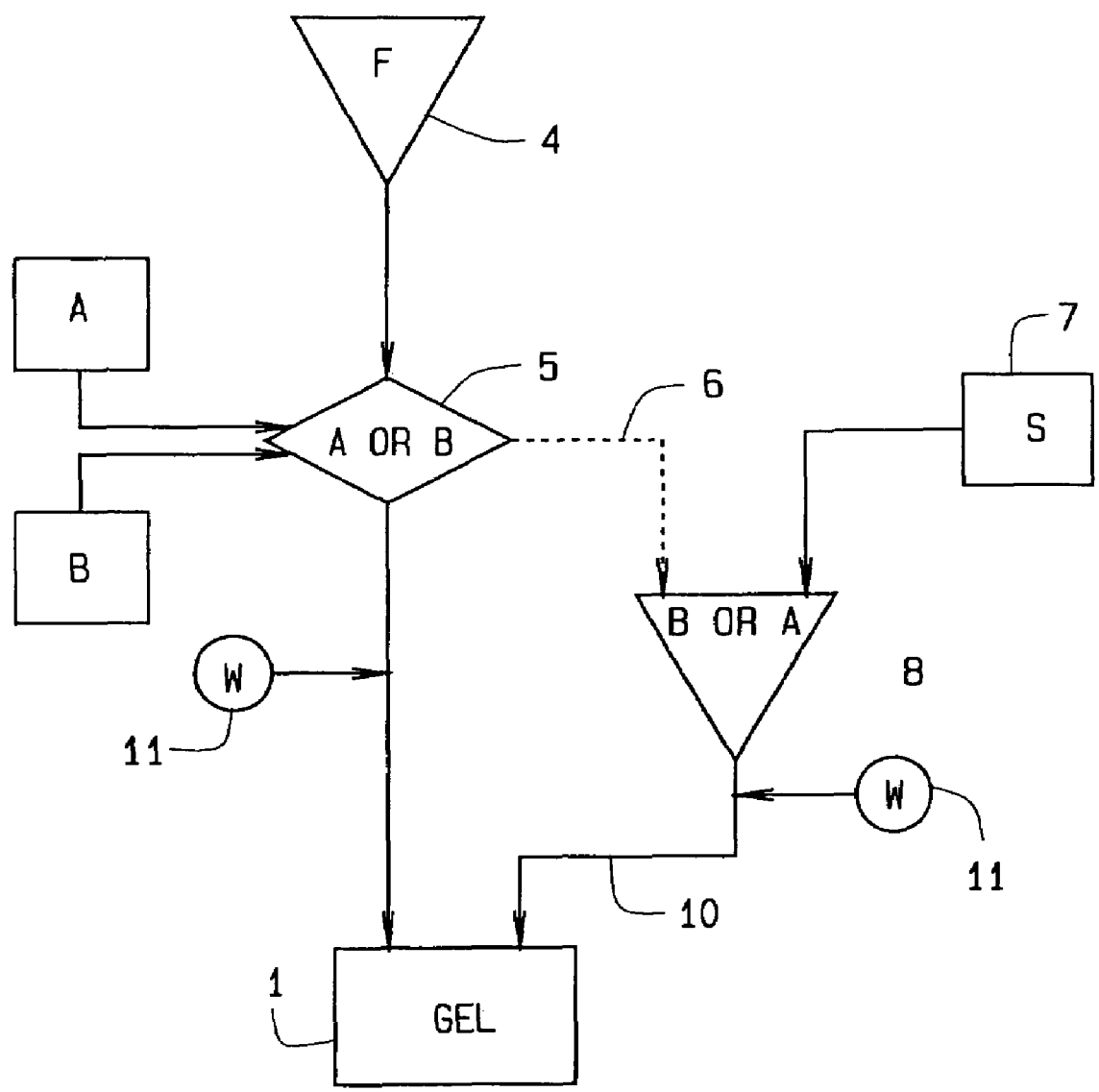
FIG. 1 shows a block diagram of the components and processes of the preferred embodiment of the fragrant gel polymer system practiced in accordance with the principles of the present invention.

The present art overcomes the prior art limitations by assembling a fragrance formulation from its components then mixing the fragrance with only one of two classes of polymer, dissolving the other class of polymer with a solvent, and then mixing the polymer carrying the fragrance with the dissolved polymer resulting in a gel product with minimal syneresis and a shortened setting time. Though the components of the invention are few in number, the sequence of mixing forms the key to the present invention. Turning to FIG. 1, a block diagram shows the fragrant gel polymer system from initial components to the resulting product.

The present invention 1 begins with the components of a fragrance formulation selected by a fragrance house or manufacturer. A fragrance may have as many components as determined by the designers and chemists of the fragrance house. The present invention then mixes the components to form the fragrance F, generally in a liquid state, as at 4.

The fragrance is then mixed with either a polymer, as at A, or a cross-linking agent, as at B, with the mixing step shown as at 5. The polymer derives from butadiene, isoprene or chloroprene. Preferably the polymer, as at A, is maleinized polybutadiene of at least 5000 molecular weight. Alternatively, the polymer includes maleinized polyisoprene of at least 200,000 molecular weight. These polymers are readily available from commercial chemical sources. A preferred polymer is Lithene® by Synthomer®, typically Lithene® N4-9000 10MA, which is a maleinized polybutadiene of a 9000 molecular weight before maleinization. The other component, a cross-linking agent comes from the amine family of polymers, including polypropoxy diamines, polypropoxy triamines and polyethoxydiamines. A preferred cross-linking agent, as at B, is Jeffamine® by Huntsman® Corp., such as the Jeffamine® D-400, which is polyetheramine. In a liquid state, the fragrance is then blended with either a polymer or a cross-linking agent. The fragrance carrying polymer then proceeds for further manufacturing as at 9.

Segregated from the fragrance carrying polymer, the polymer or cross linking agent not used in the preceding mixing step, as at 6, is next blended as at 8 with a solvent 7. Blended with the solvent, the non-fragrance carrying polymer becomes a homogeneous liquid. Preferably the solvent is benzyl benzoate. Alternatively, the solvent includes di-ethyl phthalate, di-propylene glycol, isopropyl myristate, alcohol, mineral oil, and the like. The solvents solely modify the viscosity of the non-fragrance carrying polymer and prepare it for mixing with the fragrance carrying polymer, 5, to form a gel.

Alternatively, either the polymer or the cross-linking agent undergoes further preparation for mixing with surfactants and wetting agents W, as at 11. The surfactants and wetting agents provide for integration of the polymer and the cross-linking agent with less energy and time required and for complete mixing of the fragrance within the polymer and the cross-linking agent once combined together. The preferred surfactant is Steol® from Stepan® Co. also known as ammonium laureth sulfate. The surfactants and wetting agents can be introduction either to the fragrance carrying polymer or the non-fragrance carrying polymer.

With the fragrance carrying polymer prepared as at 9 and the non-carrying fragrance polymer ready as at 10, the liquid fragrance carrying polymer is blended with the liquid non-fragrance carrying polymer in a mold to a desired shape, often an air freshener or fragrance sample, thus the present invention forms a gel product 1.

From the aforementioned description, a fragrant gel polymer system has been described. The system is uniquely capable of combining all of the fragrance components with either a polymer or a cross-linking agent in liquid form and then mixing the fragrance carrying polymer with the non-fragrance carrying polymer to make a gel product providing a fragrance. The system may be manufactured from many materials, including but not limited to, Lithene®, Jeffamine®, polymers, ferrous and non-ferrous metal foils and their alloys, and composites.

I claim:

1. A process for preparing a fragrant gel comprising the steps of:
    blending a liquid mixture A including a fragrance oil and one of a polymer or a cross linking agent;
    wherein said polymer is derived from one of maleinized butadiene, isoprene or chloroprene;
    wherein said cross linking agent is derived from one of amine or polyetheramine;
    blending a liquid mixture B including the polymer or the cross linking agent omitted from mixture A and a solvent, said mixture B being homogeneous and without any of said fragrance oil;
    wherein said solvent is one of benzyl benzoate, di-ethyl phthalate, di-propylene glycol, or isopropyl myristate, said solvent solely modifying the viscosity of mixture B;
    adding one of ammonium laureth sulfate and a wetting agent to either mixture A or mixture B;
    blending mixture A with mixture B; and,
    forming a gel carrying the fragrance following said blending of mixture A with mixture B with a minimum of syneresis;
    wherein said process reduces premature reaction of said polymer and said cross-linking agent;
    wherein said process produces a fragrance carrying gel that remains together as a whole.

2. The fragrant gel preparing process of claim 1 further comprising:
    providing a substrate having at least one recess; and,
    said forming a gel occurring in a recess of a substrate.

* * * * *